United States Patent [19]

Horstmann et al.

[11] 4,256,749

[45] Mar. 17, 1981

[54] FLUORINE-CONTAINING 1,4-DIHYDROPYRIDINE COMPOUNDS, PHARMACEUTICAL COMPOSITIONS THEREOF AND THEIR MEDICINAL USE

[75] Inventors: Harald Horstmann; Friedrich Bossert; Arend Heise; Stanislav Kazda, all of Wuppertal, Fed. Rep. of Germany

[73] Assignee: Bayer Aktiengesellschaft, Leverkusen, Fed. Rep. of Germany

[21] Appl. No.: 74,048

[22] Filed: Sep. 10, 1979

[30] Foreign Application Priority Data

Sep. 25, 1978 [DE] Fed. Rep. of Germany ....... 2841667

[51] Int. Cl.$^3$ .................... A61K 31/44; C07D 213/55
[52] U.S. Cl. .................................... 424/251; 424/258; 424/263; 546/321; 546/283; 546/284; 546/263; 546/167; 544/331; 544/333

[58] Field of Search ............... 546/321, 283, 284, 263, 546/167; 544/331, 333; 424/251, 258, 263

[56] References Cited

U.S. PATENT DOCUMENTS

| 4,044,141 | 8/1977 | Bossert et al. | 546/321 |
|---|---|---|---|
| 4,145,432 | 3/1979 | Sato | 546/283 |

*Primary Examiner*—Henry R. Jiles
*Assistant Examiner*—Robert T. Bond
*Attorney, Agent, or Firm*—Sprung, Felfe, Horn, Lynch & Kramer

[57] ABSTRACT

The invention relates to fluorine-containing 1,4-dihydropyridine compounds and method for their preparation. Also included are compositions containing said fluorine-containing 1,4-dihydropyridine compounds and the use of said compounds and compositions as agents for influencing circulation.

19 Claims, No Drawings

FLUORINE-CONTAINING 1,4-DIHYDROPYRIDINE COMPOUNDS, PHARMACEUTICAL COMPOSITIONS THEREOF AND THEIR MEDICINAL USE

The present invention relates to certain new fluorine-containing 1,4-dihydropyridine compounds, to a process for their production and to their use as agents which influence the circulation.

It has already been disclosed that 1,4-dihydropyridinecarboxylic acid esters which have interesting properties with respect to their influence on the circulation are obtained by reacting aldehydes with β-ketocarboxylic acid esters and enaminocarboxylic acid esters (compare German Offenlegungsschrift (German Published Specification) No. 2,117,571 and German Offenlegungsschrift (German Published Specification) No. 2,117,573). Dihydropyridine derivatives which contain perfluorinated carbon atoms in their ester groups, as do the compounds of the present invention, have not been described hitherto.

According to the present invention there are provided compounds which are fluorine-containing 1,4-dihydropyridines of the formula

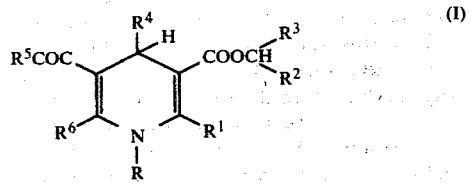

or a salt thereof, in which,

R denotes a hydrogen atom or an optionally substituted alkyl or aralkyl group, $R^1$ and $R^6$ are identical or different and each denotes an optionally substituted alkyl group, $R^4$ denotes an alkyl group, an aryl radical which is optionally substituted by 1 or 2 identical or different substituents selected from nitro, cyano, trifluoromethyl, halogen, azido, trifluoromethoxy, alkyl, alkoxy, alkylmercapto and $SO_2$-alkyl, or denotes a quinolyl, pyridyl, pyrimidyl, thienyl or furyl radical which is optionally substituted by alkyl or halogen, $R^5$ denotes an alkyl group which is optionally substituted by halogen, or denotes an alkenyl, alkynyl, alkoxyalkyl or aminoalkyl group, it being possible for the two hydrogen atoms of the amino group to be replaced by 1 or 2 alkyl groups and/or by an aralkyl group, or denotes a radical of the formula

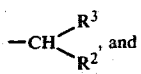

$R^2$ and $R^3$ in each case are identical or different and either one of the two substituents denotes a hydrogen atom and the other substituent denotes, or the two substituents denote, a straight-chain, branched or cyclic aliphatic hydrocarbon radical which contains at least 1 perfluorinated carbon atom with 2 or 3 fluorine substituents, this hydrocarbon radical optionally being interrupted by the grouping —$CH_2$—X—$CH_2$—, in which X denotes oxygen or sulphur, or in which $R^2$ and $R^3$ together with the CH group complete a saturated isocyclic ring which has 4 to 7 ring members and contains at least 1 perfluorinated carbon atom and is optionally substituted by an alkyl group, it being possible for this alkyl group, in turn, again to contain 1 or 2 perfluorinated carbon atoms.

Unless otherwise indicated herein alkyl, alkoxy, alkylmercapto, alkylamino, alkenyl and alkinyl substituents preferably contain up to 8 carbon atoms, and each alkyl portion in alkoxyalkyl substituents contains up to 8 carbon atoms; aralkyl substituents are preferably mono- or bi-cyclid carbocyclic in the aryl portion; (e.g. phenyl, biphenyl, naphthyl) acid contain up to 8, more preferably up to 2 carbon atoms in the alkyl portion; halogen substituents are preferably chlorine, bromine and fluorine and cyclic aliphatic substituents having at least 1 perfluorinated carbon atom contain 4 to 7 ring members.

According to the present invention we further provide a process for the production of compounds of the present invention in which (a) 1 mol of an enamine of the general formula

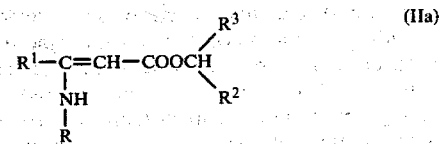

in which R, $R^1$, $R^2$ and $R^3$, have the above-mentioned meanings, is reacted with one mol of a β-ketocarboxylic acid ester of the general formula $$R^6-CO-CH_2-COOR^5 \qquad (IIIa)$$

in which $R^5$ and $R^6$ have the above-mentioned meanings, and with one mol of an aldehyde of the general formula $$R^4-CHO \qquad (IV)$$

in which $R^4$ has the above-mentioned meaning, optionally after isolation of the ylidene compound which forms from the compounds of formulae (IIIa) and (IV) and has the general formula

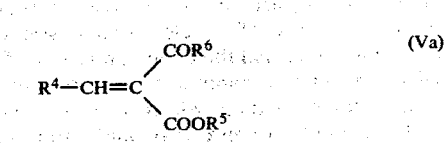

in which $R^4$, $R^5$ and $R^6$ have the above-mentioned meanings, or (b) 1 mol of an enamine of the general formula

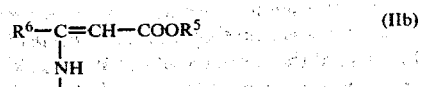

in which R, $R^5$ and $R^6$ have the above-mentioned meanings, is reacted with one mol of a β-ketocarboxylic acid ester of the general formula

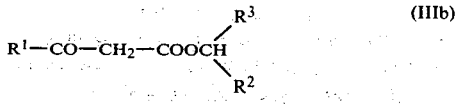

and with one mol of an aldehyde of formula (IV) as defined above, optionally after isolation of the ylidene compound which forms from the compounds of formula (IIIb) and (IV) and has the general formula

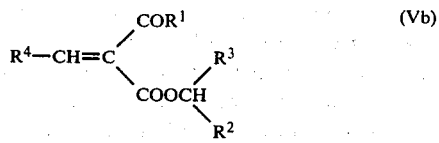

Processes (a) and (b) are optionally carried out in the presence of water or inert organic solvents, and optionally at temperatures between 20° and 150° C.

If the compounds of the present invention carry a basic substituent, these compounds can be converted with suitable organic or inorganic acids to their salts. A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxyethanesulfonic, ethylenesulfonic, benzenesulfonic, halogenobenzenesulfonic, toluensulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The compounds of the present invention and their pharmaceutically acceptable acid addition salts display powerful pharmacological actions. In particular, they are distinguished by actions on the circulation and can preferably be used as coronary agents, antihypertensive agents and agents for increasing the peripheral blood flow. Because of their novel structure and especially because of the presence of perfluorinated carbon atoms, the compounds according to the invention possess advantageous actions. Their use thus represents an advance in pharmacy.

The enamines of the general formulae (IIa) and (IIb) which can be used according to the invention are known or can be prepared by known methods from the corresponding β-diketo compounds and amines (compare A. Pinner B 34, 4239/40 (1901)).

Examples which may be mentioned are: 2-trifluoroethyl β-aminocrotonate, 2,2-hexafluoro-isopropyl β-aminocrotonate, 2-trifluoromethylisopropyl β-aminocrotonate, 3,4-penta-fluorobutyl β-aminocrotonate, 4-trifluoro-methyl-cyclohexyl β-aminocrotonate, 2-trifluoroethoxy-ethyl β-aminocrotonate, methyl β-aminocrotonate, ethyl β-aminocrotonate, isopropyl β-aminocrotonate, 2-benzylaminoethyl β-aminocrotonate, 2-chloroethyl β-aminocrotonate, 2-methoxymethyl β-aminocrotonate, 2-methylmercaptoethyl β-aminocrotonate, cyclohexyl β-aminocrotonate, allyl β-aminocrotonate, propargyl β-aminocrotonate and tetrahydrofurfuryl β-aminocrotonate.

The β-ketocarboxylic acid esters of the general formulae (IIIa) and (IIIb) which can be used according to the invention are known or can be prepared by known methods (compare Houben-Weyl, Methoden der organischen Chemie (Methods of Organic Chemistry), VII/4, 230 et seq. (1968)).

Examples which may be mentioned are: methyl acetoacetate, ethyl acetoacetate, isopropyl acetoacetate, hexyl acetoacetate, benzyl acetoacetate, cyclohexyl acetoacetate, 2-morpholinoethyl acetoacetate, 2-dimethylamino-ethyl acetoacetate, 3-diethylamino-propyl acetoacetate, 2-methoxyethyl acetoacetate, 2-ethoxyethyl acetoacetate, 2-isopropoxyethyl acetoacetate, 2-methylmercapto-ethyl acetoacetate, 2-benzylaminoethyl acetoacetate, 2-(α-methylbenzyl)-aminoethyl acetoacetate, 2-(α-methylphenethyl)-aminoethyl acetoacetate, trifluoroethyl acetoacetate, 2-trifluoroisopropyl acetoacetate, 2,2-hexafluoroisopropyl acetoacetate, 3,4-pentafluorobutyl acetoacetate, 3-trifluoromethyl-propenyl acetoacetate, 4-trifluoromethyl-cyclohexyl acetoacetate, 2-trifluoroethoxy-ethyl acetoacetate and 2-trifluoroethylmercapto-ethyl acetoacetate.

The aldehydes of the formula IV which can be used according to the invention are known or can be prepared by known methods (compare E. Mosettig, Org. Reactions VIII, 218 et seq. (1954)).

Examples which may be mentioned are: acetaldehyde, benzaldehyde, o-nitrobenzaldehyde, m-nitrobenzaldehyde, o-fluorobenzaldehyde, o-chlorobenzaldehyde, m-chlorobenzaldehyde, m-fluorobenzaldehyde, o-trifluoromethylbenzaldehyde, m-trifluoromethylbenzaldehyde, o-methylbenzaldehyde, m-methylbenzaldehyde, o-methoxybenzaldehyde, m-methoxybenzaldehyde, o-trifluoroethoxybenzaldehyde, m-trifluoroethoxybenzaldehyde, o-methylmercaptobenzaldehyde, m-methylmercaptobenzaldehyde, o-cyclopropylbenzaldehyde, o-azidobenzaldehyde, β-azidobenzaldehyde, α-pyridylaldehyde, β-pyridylaldehyde, α-furfurol, β-furfurol, thiophene-1-aldehyde, thiophene-2-aldehyde, pyrimidine-5-aldehyde, 4-methyl-pyrimidine-5-aldehyde, quinoline-2-aldehyde, naphthalene-1-aldehyde and naphthalene-2-aldehyde.

Diluents which can be used are water and all inert organic solvents. These preferably include alcohols, such as ethanol, methanol, isopropanol, ethers, such as dioxane, diethyl ether, tetrahydrofurane, glycol monomethyl ether and glycol dimethyl ether, or glacial acetic acid, dimethylformamide, dimethylsulphoxide, acetonitrile and pyridine.

The reaction temperatures can be varied within a relatively wide range. In general, the reaction is carried out at between 20° and 150° C. and preferably at the boiling point of the particular solvent.

The reaction can be carried out under normal pressure, but also under elevated pressure. In general, the reaction is carried out under normal pressure.

Compounds according to the present invention which are of particular interest are those of formula (I) in which R denotes a hydrogen atom, an alkyl group with 1 or 2 carbon atoms or a benzyl radical, $R^1$ and $R^6$ are identical or different and denote alkyl groups with 1 to 4 carbon atoms, $R^4$ denotes a phenyl radical, which is optionally substituted by one or two substituents selected from nitro, cyano, trifluoromethyl, halogen, azido, trifluoromethoxy, alkyl, alkoxy, alkylmercapto and $SO_2$-alkyl, in each case with 1 or 2 carbon atoms in the alkyl and alkoxy radicals, or denotes a pyridyl radical, $R^5$ denotes an alkyl group with 1 to 6 carbon atoms, which is optionally substituted by halogen, or denotes an alkoxyalkyl, alkenyl or alkynyl group with up to 6 carbon atoms or denotes an aminoalkyl group with 1 to 4 carbon atoms in the alkyl radical, it being possible for the two hydrogen atoms of the amino group to be replaced by 1 or 2 alkyl groups with 1 to 4 carbon atoms and/or by a benzyl group, or denotes a radical of the formula

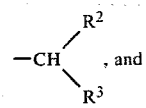

and $R^2$ and $R^3$ in each case are identical or different and either one of the two substituents denote hydrogen and the other substituent denotes, or the two substituents denote, a straight-chain, branched or cyclic alkyl radical which has up to 8 carbon atoms and preferably up to 6 carbon atoms and contains 1, 2 or 3 perfluorinated carbon atoms with, in each case, 2 or 3 fluorine substituents, this alkyl radical being optionally interrupted by the grouping $-CH_2-X-CH_2-$, in which X denotes oxygen or sulphur, or in which $R^2$ and $R^3$ together with the CH group completes a saturated isocyclic radical which has 4 to 7 ring members and contains 1, 2 or 3 perfluorinated carbon atoms and is optionally substituted by an alkyl group with 1 to 4 carbon atoms, it being possible for this alkyl group, in turn, again to contain one or two perfluorinated carbon atoms.

In addition to those mentioned in the Examples, the following compounds according to the invention may also be singled out:

| $R^1$ | $R^2$ | $R^3$ | $R^4$ |
|---|---|---|---|
| H | $CF_3-CH_2$ | 2-Cl-phenyl | $-CH_2-CH_2-N(CH_3)_2$ |
| H | $CF_3-CH_2$ | 2-Cl-phenyl | $-CH_2-CH_2-N(CH_3)-CH_2-C_6H_5$ |
| H | $CF_3-CH_2$ | 2-$CF_3$-phenyl | $-CH_2-CH_2-N(CH_3)-CH(CH_3)-C_6H_5$ |
| H | $CF_3-CH_2$ | 2-$NO_2$-phenyl | $-CH_2-CH_2-N(CH_3)_2$ |
| H | $CF_3-CH_2-$ | 2-$NO_2$-phenyl | $-CH_2-CH_2-N(CH_3)-CH(CH_3)-C_6H_5$ |
| $CH_3-$ | $CF_3-CH_2-$ | 2-Cl-phenyl | $-CH_3$ |
| $C_6H_5CH_2-$ | $CF_3-CH_2-$ | 2-$CF_3$-phenyl | $-C_2H_5$ |
| H | $(CF_3)_2CH-$ | 2-Cl-phenyl | $-CH_2-CH_2-SCH_3$ |
| H | $(CF_3)_2CH-$ | 2-$NO_2$-phenyl | $-CH_2-CH_2-Cl$ |

-continued

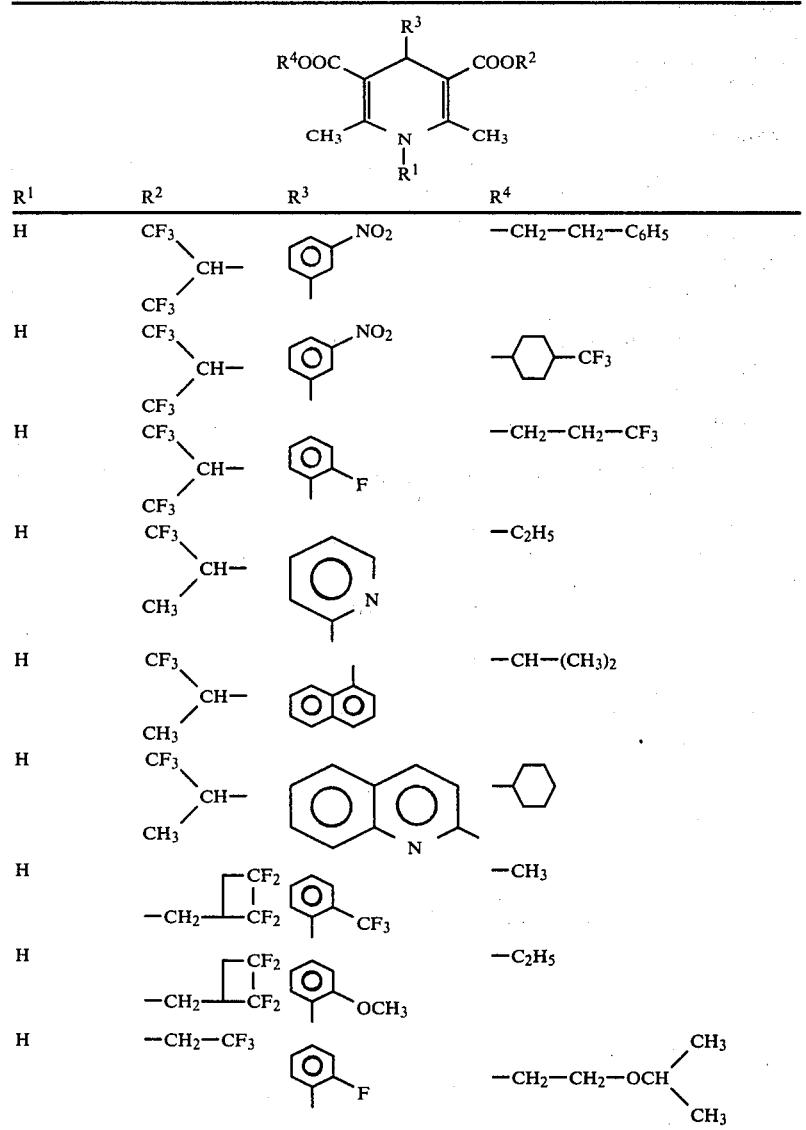

The new compounds are substances which can be used as medicaments. They have a broad and diverse pharmacological action spectrum. In detail, the following main actions are demonstrable in animal experiments:

1. On parenteral, oral and perlingual administration the compounds produce a distinct and long-lasting dilation of the coronary vessels.

This action on the coronary vessels is intensified by a simultaneous nitrite-like effect of reducing the load on the heart.

They influence or modify the heat metabolism in the sense of an energy saving.

2. The excitability of the stimulus formation and excitation conduction system within the heart is lowered, so that antifibrillation action demonstrable at therapeutic doses results.

3. The tone of the smooth muscles of the vessels is greatly reduced under the action of the compounds. This vascular-spasmolytic action can take place in the entire vascular system or can manifest itself more or less isolated in circumscribed vascular regions (such as, for example, the central nervous system).

4. The compounds lower the blood pressure of hypertonic animals and can thus be used as antihypertensive agents.

5. The compounds have strongly muscular-spasmolytic actions which manifest themselves on the smooth muscle of the stomach, the intestinal tract, the urogenital tract and the respiratory system.

As stated above, the invention also relates to the use in medicine of the compounds of the invention.

The present invention provides pharmaceutical composition containing as active ingredient a compound of the invention in admixture with a solid, liquid or liquefied gaseous diluent.

The invention further provides pharmaceutical compositions containing as active ingredient a compound of the invention in the form of a sterile and/or physiologically isotonic aqueous solution.

The invention also provides medicaments in dosage unit form comprising a compound of the invention.

The invention also provides medicaments in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in micro-encapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.5 to 90% of the active ingredient by weight of the total composition.

In addition to a compound of the invention, the pharmaceutical compositions and medicaments and according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for intravenous administration of the medicaments of the invention is 0.25 to 5 mg of active ingredient, and for oral administration is 2.5 to 250 mg of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), or rectally, preferably orally or parenterally, especially perlingually or intravenously. Preferred pharmaceutical compositions and medicaments are therefore those adapted for administration such as oral or parenteral administration. Administration in the method of the invention is preferably oral or parenteral administration.

In general it has proved advantageous to administer intravenously amounts of from 0.001 mg to 1 mg/kg, preferably 0.005 to 0.1 mg/kg, of body weight per day and to administer orally amounts of from 0.005 mg to 10 mg/kg, preferably 0.05 to 5 mg/kg, of body weight per day, to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples illustrate the preparation of compounds of the present invention.

EXAMPLE 1

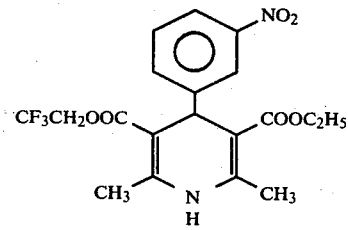

3-Ethoxycarbonyl-2,6-dimethyl-4-(3-nitrophenyl)-5-trifluoroethoxycarbonyl-1,4-dihydropyridine.

5 g of trifluoroethyl aminocrotonate in 500 ml of ethanol are heated with 7.3 g of ethyl m-nitrobenzylidineacetoacetate for 3 hours under reflux. The reaction mixture is cooled and filtered and 7.8 g, corresponding to 67% of theory, of pale yellow crystals with a melting point of 192° C. are obtained.

EXAMPLE 2

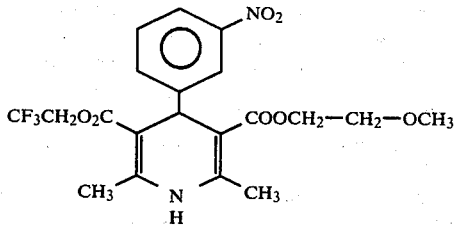

2,6-Dimethyl-3-$\beta$-methoxyethoxycarbonyl-4-(3-nitrophenyl)-5-trifluoroethoxycarbonyl-1,4-dihydropyridine.

5 g of trifluoroethyl aminocrotonate are heated together with 3.1 g of $\beta$-methoxyethyl m-nitrobenzylideneacetoacetate in 500 ml of propanol for 3 hours under reflux. The reaction mixture is filtered and 9.3 g, corresponding to 74% of theory, of pale yellow crystals with a melting point of 169° C. are obtained.

The compounds listed in the table were obtained by a procedure analogous to Example 1.

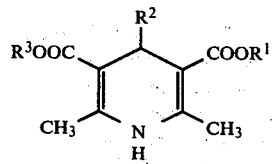

| No. | $R^1$ | $R^2$ | $R^3$ | Melting Point | Remarks |
|---|---|---|---|---|---|
| 3 | $CH_3$ | (3-nitrophenyl) | $CF_3-CH_2-$ | 161° C. | |
| 4 | $C_2H_5$ | " | " | 158° C. | |
| 5 | $CH_3-$ | (3-nitrophenyl, O₂N) | " | 153° C. | |
| 6 | " | " | $(CF_3)_2-CH-$ | 165° C. | |
| 7 | $nC_3H_7-$ | " | $CF_3-CH_2-$ | 172° C. | |
| 8 | $isoC_3H_7-$ | " | " | 158° C. | |
| 9 | cyclopropyl | " | " | 178° C. | |
| 10 | $isoC_3H_7-$ | " | $CH_2-CH_2-O-CH_2CF_3$ | — | Oily, purified by chromatography, M⁺ 486 |
| 11 | $CF_3-CH_2-$ | (3-nitrophenyl) | $CF_3-CH_2-$ | 209° C. | |

-continued $$\begin{array}{c} R^2 \\ R^3OOC \diagdown \diagup COOR^1 \\ CH_3 \diagup N \diagdown CH_3 \\ H \end{array}$$

| No. | $R^1$ | $R^2$ | $R^3$ | Melting Point | Remarks |
|---|---|---|---|---|---|
| 12 | " | 2-Cl-phenyl | " | 95° C. | |
| 13 | $CH_3$ | " | " | 119° C. | |
| 14 | $C_2H_5-$ | " | " | | Oily, purified by chromatography, single compound according to thin layer chromatography, |
| 15 | $CH_3-$ | 2-$CF_3$-phenyl | " | 114° C. | |
| 16 | $CF_3-CH_2-$ | " | " | 131° C. | M⁻ 417 |
| 17 | " | 2-$CH_3$-phenyl | " | 119° C. | |
| 18 | " | 2-$NO_2$-phenyl | " | 134° C. | |
| 19 | " | 2-$OCH_3$-phenyl | " | 114° C. | |

Among the new 1,4-dihydropyridine salts of the invention, those salts that are pharmaceutically acceptable are particularly important and are preferred.

The new free 1,4-dihydrpyridines of the general formula I and their salts can be interconverted in any suitable manner; methods for such interconversion are known in the art.

The present invention also comprises pharmaceutically acceptable bioprecursors of the active compounds of the present invention.

For the purposes of this Specification the term 'pharmaceutically acceptable bioprecursor' of an active compound of the invention means a compound having a structural formula different from the active compound but which nonetheless, upon administration to a warm-blooded animal is converted in the animal's body to the active compound.

We claim:

1. A fluorine-containing 1,4-dihydropyridine of the formula

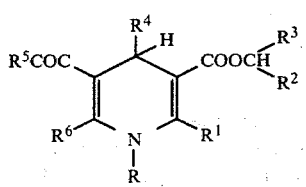

(I)

or a salt thereof, in which

R denotes a hydrogen atom an alkyl group having up to 8 carbon atoms or an aralkyl group which is monocyclic or bicyclic carbocyclic in the aryl portion and contains up to 8 carbon atoms in the alkyl portion, $R^1$ and $R^6$ identical or different and each denotes an alkyl group having up to 8 carbon atoms, $R^4$ represents alkyl having up to 8 carbon atoms or represents a monocyclic or bicyclic carbocyclic aryl radical which is optionally substituted by 1 or 2 identical or different substituents selected from nitro, cyano, trifluoromethyl, halogen, azido, trifluoromethoxy, alkyl, alkoxy, alkylmercapto and $SO_2$—alkyl, each of said alkyl, alkoxy, alkylmercapto and $SO_2$—alkyl groups having up to 8 carbon atoms, or denotes a quinolyl, pyridyl, pyrimidyl, thienyl or furyl radical which is optionally substituted by alkyl having up to 8 carbon atoms or halogen, $R^5$ denotes an alkyl group having up to 8 carbon atoms which is optionally substituted by halogen, or denotes an alkenyl, alkynyl, alkoxyalkyl or aminoalkyl group, each having up to 8 carbon atoms, it being possible for the two hydrogen atoms of the amino group to be replaced by 1 or 2 alkyl groups each having up to 8 carbon atoms and/or by an aralkyl group as defined above for R, or denotes a radical of the formula

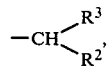

and

R² and R³ in each case are identical or different and either one of the two substituents denotes a hydrogen atom and the other substituent denotes, or each of the two substituents denotes, a straight-chain, branched or cyclic radical group having up to 8 carbon atoms or an aralkyl group which is monocyclic or bicyclic carbocyclic in the aryl portion and contains up to 8 carbon atoms in the alkyl portion which contains at least 1 perfluorinated carbon atom having 2 or 3 fluorine substituents, this alkyl radical optionally being interrupted by the group —CH₂—X—CH₂—, in which X denotes oxygen or sulphur, or in which R² and R³ together with the CH group complete a saturated isocyclic ring which has 4 to 7 ring members and contains at least 1 perfluorinated carbon atom and is optionally substituted by an alkyl group, it being possible for this alkyl group, in turn, again to contain 1 or 2 perfluorinated carbon atoms.

in which

X denotes oxygen or sulphur, or in which

R² and R³ together with the CH group completes a saturated isocyclic radical which has 4 to 7 ring members and contains 1, 2 or 3 perfluorinated carbon atoms and is optionally substituted by an alkyl group with 1 to 4 carbon atoms, it being possible for this alkyl group, in turn, again to contain one or two perfluorinated carbon atoms.

2. A compound according to claim 1, in which

R denotes a hydrogen atom, an alkyl group with 1 or 2 carbon atoms or a benzyl radical, R¹ and R⁶ are identical or different and each denotes an alkyl group with 1 to 4 carbon atoms, R⁴ denotes a phenyl radical, which is optionally substituted by one or two substituents selected from nitro, cyano, trifluoromethyl, halogen, azido, trifluoromethoxy, alkyl, alkoxy, alkylmercapto and SO₂—alkyl, in each case with 1 or 2 carbon atoms in the alkyl and alkoxy radicals, or denotes a pyridyl radical, R⁵ denotes an alkyl group with 1 to 6 carbon atoms, which is optionally substituted by halogen, or denotes an alkoxyalkyl, alkenyl or alkynyl group with up to 6 carbon atoms or denotes an aminoalkyl group with 1 to 4 carbon atoms in the alkyl radical, it being possible for the two hydrogen atoms of the amino group to be replaced by 1 or 2 alkyl groups with 1 to 4 carbon atoms and/or by a benzyl group, or denotes a radical of the formula

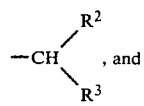, and and

R² and R³ in each case are identical or different and either one of the two substituents can denote hydrogen and the other substituent denotes, or the two substituents denote, a straight-chain, branched or cyclic alkyl radical which has up to 8 carbon atoms and contains 1, 2 or 3 perfluorinated carbon atoms with in each case, 2 or 3 fluorine substituents, this alkyl radical being optionally interrupted by the grouping —CH₂—X—CH₂—, in which X denotes oxygen or sulphur, or in which R² and R³ together with the CH group completes a saturated isocyclic radical which has 4 to 7 ring members and contains 1, 2 or 3 perfluorinated carbon atoms and is optionally substituted by an alkyl group with 1 to 4 carbon atoms, it being possible for this alkyl group, in turn, again to contain one or two perfluorinated carbon atoms.

3. A compound according to claim 2, in which R² and/or R³ denote a straight-chain, branched or cyclic alkyl radical with having up to 6 carbon atoms, and contains 1, 2 or 3 perfluorinated carbon atoms with having in each case, 2 or 3 fluorine substituents, said alkyl radical being optionally interrupted by the grouping —CH₂—X—CH₂— in which X denotes oxygen or sulphur.

4. A compound according to claim 1 or 2 wherein each halogen is chlorine bromine or fluorine.

5. A pharmaceutical composition containing as an active ingredient a circulation influencing amount of compound according to claim 1 in admixture with a solid liquid or liquefied gaseous diluent.

6. A pharmaceutical composition of claim 5 containing as an active ingredient a circulation influencing amount of a compound according to claim 5 in the form of a sterile or physiologically isotonic aqueous solution.

7. A composition according to claim 5 containing from 0.5 to 90% by weight of the said active ingredient.

8. A medicament in dosage unit form comprising a circulation influencing amount of a compound according to claim 1 together with an inert pharmaceutical carrier.

9. A medicament of claim 8 in the form of tablets, pills, dragees, capsules, ampoules, or suppositories.

10. A method of combating circulatory diseases in warm-blooded animals which comprises administering to the animals a circulation influencing amount of an active compound according to claim 1 either alone or in admixture with a diluent or in the form of a medicament.

11. A method according to claim 10 in which the active compound is administered intravenously in an amount of 0.001 to 1 mg per kg body weight per day.

12. A method according to claim 10 in which the active compound is administered intravenously in an amount of 0.005 to 0.1 mg per ky body weight per day.

13. A method according to claim 10 in which the active compound is administered orally in an amount of 0.005 to 10 mg per kg body weight per day.

14. A method according to claim 10 in which the active compound is administered orally in an amount of 0.05 to 5 mg per ky body weight per day.

15. A compound according to claim 1 which is 3-ethoxycarbonyl-2,6-dimethyl-4-(3-nitrophenyl)-5-trifluoroethoxycarbonyl-1,4-dihydropyridine.

16. A compound according to claim 1 which is 2,6-dimethyl-3-β-methoxyethoxycarbonyl-4-(3-nitrophenyl)-5-trifluoroethxycarbonyl-1,4-dihydropyridine.

17. A compound according to claim 1 which is 2,6-dimethyl-3,5-bis-trifluoroethoxycarbonyl-4-(3-nitrophenyl)-1,4-dihydropyridine.

18. A compound according to claim 1 which is 2,6-dimethyl-3,5-bis-trifluoroethoxycarbonyl-4-(2-trifluorophenyl)-1,4-dihydropyridine.

19. A compound according to claim 1 which is 2,6-dimethyl-3-methoxycarbonyl-4-(2-trifluorophenyl)-5-trifluoroethoxycarbonyl-1,4-dihydropyridine.

* * * * *

UNITED STATES PATENT AND TRADEMARK OFFICE
CERTIFICATE OF CORRECTION

PATENT NO. : 4,256,749
DATED : Mar. 17, 1981
INVENTOR(S) : Harald Horstmann et al It is certified that error appears in the above—identified patent and that said Letters Patent is hereby corrected as shown below:

Column 14, line 46, Insert --are-- before "identical".

Column 15, line 40, Delete "with" and insert --having--.

Column 15, line 43, Delete "with" and insert --having--.

Column 15, line 48, Delete "with" and insert --having--.

Column 15, line 51, Delete "with" and insert --having--.

Column 15, line 54, Delete "with" and insert --having--.

Column 15, line 55, Delete "with" and insert --having--.

Column 15, line 58, Delete "with" and insert --having--.

Column 15, line 68, Delete "can denote" and insert --denotes--.

Signed and Sealed this

Eleventh Day of August 1981

[SEAL]

Attest:

GERALD J. MOSSINGHOFF

Attesting Officer

Commissioner of Patents and Trademarks